United States Patent
Gates et al.

(10) Patent No.: US 8,538,207 B2
(45) Date of Patent: Sep. 17, 2013

(54) METHOD OF FABRICATING WAVEGUIDE DEVICES WHICH USE EVANESCENT COUPLING BETWEEN WAVEGUIDES AND GROOVES

(75) Inventors: James Christopher Gates, Southampton (GB); Corin Barry Edmund Gawith, Southampton (GB); Peter George Robin Smith, Romsey (GB)

(73) Assignee: University of Southampton, Southampton (GB)

( * ) Notice: Subject to any disclaimer, the term of this patent is extended or adjusted under 35 U.S.C. 154(b) by 747 days.

(21) Appl. No.: 12/596,105

(22) PCT Filed: Mar. 20, 2008

(86) PCT No.: PCT/GB2008/000995
§ 371 (c)(1),
(2), (4) Date: Mar. 18, 2010

(87) PCT Pub. No.: WO2008/125797
PCT Pub. Date: Oct. 23, 2008

(65) Prior Publication Data
US 2010/0172610 A1    Jul. 8, 2010

(30) Foreign Application Priority Data
Apr. 16, 2007 (GB) .................................. 0707304.2

(51) Int. Cl.
*G02B 6/12* (2006.01)
*G02B 6/26* (2006.01)
*G02B 6/10* (2006.01)

(52) U.S. Cl.
USPC .............................. 385/14; 385/30; 264/1.24

(58) Field of Classification Search
USPC .............. 385/14, 30, 37, 129, 132; 264/1.27, 264/1.24
See application file for complete search history.

(56) References Cited

U.S. PATENT DOCUMENTS

| 4,781,424 A * | 11/1988 | Kawachi et al. ............... 385/132 |
| 5,784,509 A * | 7/1998 | Yamane et al. ................. 385/49 |

(Continued)

FOREIGN PATENT DOCUMENTS

| EP | 1 058 135 | 6/2000 |
| EP | 1 065 534 | 1/2001 |

(Continued)

OTHER PUBLICATIONS

International Search Report for corresponding application No. PCT/GB2008/000995 mailed on Jun. 24, 2008.

(Continued)

*Primary Examiner* — Akm Enayet Ullah
(74) *Attorney, Agent, or Firm* — Renner, Otto, Boisselle & Sklar, LLP (57) ABSTRACT

An optical waveguide device (10) comprises a planar substrate with a lower cladding layer (14), a core layer (16) and an upper cladding layer (18), a groove (20) in the substrate that extends at least into the core layer (16), and a waveguiding channel (22) in the core layer (16), wherein at least a part of the waveguiding channel (22), which may contain a Bragg grating, is sufficiently proximate to the groove (20) in the plane of the substrate for an evanescent field of light propagating in the waveguiding channel (22) to extend laterally into the groove (20). Material contained in the groove modifies the properties of the waveguiding channel, so that a sample of material can be analysed or an active material can be used to modulate the propagating light. The groove (20) can be made before the waveguide (22). The groove (20) can be made by cutting into the substrate with a saw and the waveguide (22) can be made by direct writing in the core layer (16) with an ultraviolet beam.

18 Claims, 4 Drawing Sheets

(56) References Cited

U.S. PATENT DOCUMENTS

| | | | |
|---|---|---|---|
| 6,442,312 B1* | 8/2002 | Terao et al. | 385/37 |
| 6,731,839 B2* | 5/2004 | Bhagavatula et al. | 385/37 |
| 6,801,550 B1* | 10/2004 | Snell et al. | 372/6 |
| 6,882,676 B2* | 4/2005 | Song et al. | 372/102 |
| 6,996,140 B2* | 2/2006 | Waarts et al. | 372/21 |
| 7,127,140 B2* | 10/2006 | Kobayashi et al. | 385/37 |
| 7,302,139 B1* | 11/2007 | Ames | 385/37 |
| 7,440,653 B2* | 10/2008 | Smith et al. | 385/37 |
| 7,526,156 B2* | 4/2009 | Lee et al. | 385/31 |
| 7,535,934 B2* | 5/2009 | Nicholson et al. | 372/6 |
| 7,700,908 B2* | 4/2010 | Wang et al. | 250/234 |
| 7,751,657 B2* | 7/2010 | Lee | 385/12 |
| 8,135,245 B2* | 3/2012 | Rodriguez Erdmenger et al. | 385/12 |
| 8,270,789 B2* | 9/2012 | Ogawa et al. | 385/37 |
| 2002/0191912 A1* | 12/2002 | Robinson et al. | 385/37 |
| 2002/0191934 A1* | 12/2002 | Kato et al. | 385/129 |

FOREIGN PATENT DOCUMENTS

| | | |
|---|---|---|
| EP | 1 265 086 | 12/2002 |
| EP | 1 267 182 | 12/2002 |
| EP | 1710605 | 10/2006 |
| GB | 2 353 898 | 3/2001 |
| JP | 03013906 | 1/1991 |
| JP | 05107568 | 4/1993 |
| JP | 10090543 | 4/1998 |
| WO | 93/20430 | 10/1993 |
| WO | 00/72062 | 11/2000 |
| WO | 02/01262 | 1/2002 |
| WO | 02/33457 | 4/2002 |
| WO | 2004/049024 | 6/2004 |
| WO | 2006/008447 | 1/2006 |
| WO | 2006/008448 | 1/2006 |

OTHER PUBLICATIONS

UK Intellectual Property Office Search Report for corresponding application No. GB0707304.2 dated Nov. 9, 2007.

Sparrow et al.; "Planar waveguide hygrometer and state sensor demonstrating supercooled water recognition," Sensors and Actuators B—Chemical, vol. 107(2); 2005; p. 856.

Sparrow et al.; "First order phase change detection using planar waveguide Bragg grating refractometer," Applied Physics B—Lasers and Optics, vol. 81(1); 2005; p. 1.

Sparrow et al.; "Assessment of Waveguide Thermal Response by Interrogation of UV Written Planar Gratings," IEEE Photonics Technology Letters, vol. 17(2); 2005; p. 438.

Nasu et al.; "Birefringence suppression of UV-induced refractive index with grooves in silica-based planar lightwave circuits," Electronics Letters, vol. 41 (20); 2005; p. 1118.

Inoue et al.; "Polarization Sensitivity of a Silica Waveguide Thermooptic Phase Shifter for Planar Lightwave Circuits," IEEE Photonics Technology Letters, vol. 4(1); 1992; p. 36.

Iwai et al.; "High-power blue generation from a periodically poled $MgO:LiNbO_3$ ridge-type waveguide by frequency doubling of a diode end-pumped $Nd:Y_3Al_5O_{12}$ laser," Applied Physics Letters, vol. 83 (18); Nov. 3, 2003; p. 3659.

Kurimura et al.; "Quasi-phase-matched adhered ridge waveguide in $LiNbO_3$," Applied Physics Letters, vol. 89(19), article 191123; 2006.

Mizuuchi et al.; "Efficient 340-nm light generation by a ridge-type waveguide in a first-order periodically poled $MgO:LiNbO_3$," Optics Letters, vol. 28(15); 2003; p. 1344.

Kersey et al.; "Fiber Grating Sensors," Journal of Lightwave Technology, vol. 15 (8); 1997; p. 1442.

Pan et al.; "Voltage-Controlled Optical Fiber Coupler Using a Layer of Low-Refractive-Index Liquid Crystal with Positive Dielectric Anisotropy," Japanese Journal of Applied Physics Part 1—Regular Papers, Short Notes & Review Papers, vol. 35(12A); 1995; pp. 6410-6415.

Malic et al.; "Integrated miniaturized optical detection platform for fluorescence and absorption spectroscopy," Sensors and Actuators A, vol. 135, No. 2; Apr. 4, 2007; pp. 515-524.

Sparrow et al.; "25GHz Tunability of Planar Bragg Grating using Liquid Crystal Cladding and Electric Field," Quantum Electronics and Laser Science, 2005 Conference, IEEE vol. 2; May 22, 2005; pp. 963-935.

International Preliminary Report on Patentability for corresponding application No. PCT/GB2008/000995 mailed Oct. 29, 2009.

\* cited by examiner

METHOD OF FABRICATING WAVEGUIDE DEVICES WHICH USE EVANESCENT COUPLING BETWEEN WAVEGUIDES AND GROOVES

This application is a national phase of International Application No. PCT/GB2008/000995 filed Mar. 20, 2008 and published in the English language.

BACKGROUND OF THE INVENTION

The present invention relates to evanescent field optical waveguide devices and methods for the manufacture of such devices.

A class of optical devices is known in which an optical channel waveguide is formed in a planar substrate comprising a core layer sandwiched between a lower cladding layer and an upper cladding layer. The channel waveguide is defined by a higher refractive index channel in the core layer. A window is formed in the substrate surface such that it overlies part of the waveguide, and has a depth through the upper cladding layer down to, and possibly into, the core layer. A sample of material can be placed in the window, and part of the evanescent field of light propagating in the waveguide will extend out of the waveguide and into the material in the window, where the light and the material interact to modify the optical field.

This can be utilized in a number of ways. The modification of the optical field can be used for frequency or amplitude modulation of the light. Alternatively, changes in the light can be used to infer properties of the material. Hence, these devices are generally modulators or detectors.

Often, a Bragg grating is included in the waveguide under the window. This provides a mechanism for determining the refractive index of the material via a spectral measurement. The presence of the sample affects the effective modal index experienced by light propagating in the grating and hence modifies the wavelength filtering response of the Bragg grating (it shifts the Bragg wavelength). The wavelength shift in light transmitted or reflected by the grating that is produced by the sample can be measured, and the refractive index of the material calculated from the size and direction of the shift.

Examples of sensors of this type can be found in WO 2006/008447 [1] and WO 2006/008448 [2].

A particularly useful technique for forming the channel waveguide is that of direct ultraviolet (UV) writing, as described in WO 2004/049024 [3]. In this technique, the core layer of the substrate is photosensitive to ultraviolet light. A spot of ultraviolet light is formed having a width the same as the desired width of the waveguide, the spot is positioned in the core layer, and the spot and the substrate are moved relative to each other to trace out the path of the waveguide. The ultraviolet light causes an increase in refractive index of the photosensitive material, thereby defining the waveguide. The spot may have a periodic intensity pattern of high and low intensity fringes, produced for example by intersecting two beams of light at an angle or by exposure through a phase mask. If the movement of the light spot relative to the substrate is at a constant velocity and exposure of the substrate to the spot is continuous, a uniform change in index is produced, giving a conventional waveguide. If exposure is discontinuous, a Bragg grating can be produced. Thus, the method provides a simple technique for creating waveguides having gratings therein in a single fabrication step.

Once the waveguide (including gratings if desired) has been written in the substrate, the sample window for the optical device can be formed. Conventionally, this is done by etching with hydrofluoric acid, which can remove the cladding and core layers to a desired depth [1, 2, 4-6]. Use of hydrofluoric acid is undesirable from safety, environmental and industrial points of view. Also, it is necessary that the etching be carried out after the waveguide has been written. Hence any error in the etching stage will ruin the otherwise completed substrate and waste the effort expended in writing the waveguide. Etching is also slow and relatively costly, and the versatility of the device is limited by the fact that the window must be positioned on top of the waveguide, so that only a limited range of configurations is possible. Also, the etched window has sharply defined edges across the waveguide which present abrupt changes to the propagating light, giving rise to undesirable back reflections and cavity effects.

SUMMARY OF THE INVENTION

A first aspect of the present invention is directed to a method of fabricating an optical waveguide device, comprising: providing a planar substrate comprising at least a lower cladding layer, a core layer and an upper cladding layer; and forming in the substrate: a groove having a depth extending at least into the core layer; and a waveguiding channel in the core layer; wherein at least a part of the waveguiding channel is sufficiently proximate to the groove in the plane of the substrate for an evanescent field of light propagating in the waveguiding channel to extend laterally into the groove.

This provides an evanescent optical field device with a lateral geometry, in that the waveguide and the groove are arranged side-by-side in the plane of the substrate, giving a horizontal configuration assuming the device is oriented with the substrate horizontal. This offers a range of advantages over the conventional vertical configuration of a surface window over the waveguide. For example, under the invention, the waveguide can have a curved path through the core and hence be smoothly brought into proximity with the groove. This gives an adiabatic change in the geometry and avoids the abrupt edge changes of a window that produce undesirable reflection effects. Also, the lateral configuration gives great flexibility to the relative arrangement of the waveguide and the groove. The waveguide can access the groove at multiple points, and it is straightforward to provide any amount of proximity. Further, the use of a groove instead of a surface window removes the need to use acid etching, because the groove can be formed by a variety of other simpler and less hazardous techniques.

There is substantial flexibility available for manufacturing the device. The lateral geometry allows either the waveguide or the groove to be made first. In particular, the groove may be formed before the waveguiding channel is formed. This is different from conventional window arrangements where the window must be made after the waveguide, so that the intricate effort of making the waveguide is wasted if an error occurs in making the window. The present invention allows the simple step of making the groove to be performed first so that an already written waveguide is not wasted in the event of an error.

The method may further comprise forming a Bragg grating in the part of the waveguiding channel proximate to the groove. The inclusion of a grating allows the device to perform a range of functions, such a refractive index measurement of a sample material in the groove, or tuning of the grating by modification of an active material in the groove. The method is thus versatile in allowing many different devices to be fabricated in a simple manner.

For example, the core layer may be, photosensitive, and the waveguiding channel and any Bragg grating may be formed by exposing parts of the core layer to a spot of ultraviolet light to produce a change in refractive index. Further, the spot of ultraviolet light may have a periodic intensity pattern of high and low intensity fringes. Direct writing of a waveguide with a writing spot of ultraviolet light is an attractively simple technique that allows complex waveguide configurations incorporating gratings to be created in a single fabrication step. Precise positioning of the waveguide is readily achievable, so that if the groove is formed first, using a low precision process, subsequent ultraviolet writing of the waveguide can provide the appropriate level of positional accuracy between the groove and the waveguide.

For example, if the groove is formed before the waveguiding channel is formed, the position of the spot of ultraviolet light relative to the groove in the plane of the substrate may be tested during formation of the waveguiding channel by measuring the amount of light transmitted from the spot into the groove. This is a simple technique by which the separation between the waveguide and the groove can be accurately controlled during waveguide formation.

The groove may be formed using a cutting device, such as a semiconductor wafer dicing or milling saw. Cutting a groove into the substrate is much quicker, cheaper and safer than etching a window using acid. Although cutting with a saw is a relatively coarse technique, the manufacturing tolerances on the groove are relatively low if it is formed first, because the waveguide can be subsequently written relative to the groove with appropriate accuracy. Cutting a groove after formation of the waveguide is an alternative, but the positional accuracy is more difficult to achieve.

Alternatively, the groove may be formed using a lithographic technique and etching. Lithography can be used before or after the waveguide is formed, but is a more complex process than cutting.

The groove may have a depth extending to, into or through the lower cladding layer. This gives a groove which exposes the whole thickness of the core layer. Hence the extension of the optical field into the groove is unimpeded and the interaction with material in the groove can be maximised for a given proximity. Also, the lateral geometry allows the depth of the groove to specified with a large tolerance compared to the depth of an etched window, which determines proximity to the waveguide and hence must be very accurately defined.

The device may be made more complex by including additional grooves, waveguides, gratings and/or positions of proximity between a groove and a waveguide. For example, the method may further comprise forming one or more further waveguiding channels in the core layer, wherein at least a part of the or each further waveguiding channel is sufficiently proximate to the groove in the plane of the substrate for an evanescent field of light propagating in the further waveguiding channel to extend laterally into the groove. Thus, a single groove can be accessed by multiple waveguides. Additionally, the method may further comprise forming a Bragg grating in the part of each waveguiding channel proximate to the groove.

In other embodiments, the method may further comprise forming one or more further grooves in the substrate, the or each groove having a depth extending at least into the core layer, wherein the waveguiding channel has parts sufficiently proximate in the plane of the substrate to every groove for an evanescent field of light propagating in the waveguiding channel to extend into the grooves. This gives a device in which a single waveguide can access multiple grooves, each of which may contain a different material or have a different surface treatment to react with the material. The method may further comprise forming a Bragg grating in each part of the waveguiding channel proximate to a groove.

Further, the waveguiding channel may have at least two parts sufficiently proximate to the groove in the plane of the substrate for an evanescent field of light propagating in the waveguiding channel to extend into the groove, each proximate part having a different proximity to the groove.

Also, the waveguiding channel may have at least two parts sufficiently proximate to the groove in the plane of the substrate for an evanescent field of light propagating in the waveguiding channel to extend into the groove, each proximate part having a different width.

In embodiments in which a grating is formed in the waveguiding channel, the Bragg grating may be a chirped Bragg grating, and the waveguiding channel may be formed such that the part proximate to the groove has a proximity that varies as a function of the grating period. This can be engineered so that a temperature independent refractive index measurement of a material in the groove can be obtained.

In other embodiments, the optical waveguide device may be an optical modulator, and the method may further comprise filling the groove with liquid crystal and providing the substrate with electrodes by which an electric field can be applied across the liquid crystal to modify the Bragg wavelength of the Bragg grating.

In alternative embodiments, the optical waveguide device may be a refractive index sensor, and the method may further comprise: forming a second groove in the substrate, filling the groove with liquid crystal and providing the substrate with electrodes by which an electric field can be applied across the liquid crystal; forming a second waveguiding channel arranged to collect light reflected from or transmitted by the Bragg grating in the said waveguiding channel, the second waveguiding channel having a portion sufficiently proximate to the second groove in the plane of the substrate for an evanescent field of light propagating in the second waveguide to extend laterally into the second groove; and forming a second Bragg grating in the proximate part of the second waveguiding channel such that application of an electric field across the liquid crystal can modify the Bragg wavelength of the second Bragg grating. This gives a device in which measuring the light from the second grating while that grating is tuned in wavelength allows a spectral analysis to be performed of the light from the first grating that is measuring the refractive index of any material in the groove.

Alternatively, the optical waveguide device may be a laser, and the method may further comprise: forming a pair of Bragg gratings in the waveguiding channel, one on each side of the part proximate to the groove, to define a resonant cavity in the waveguiding channel; forming a second waveguiding channel in the core layer for propagation of pump light, the second waveguiding channel having a part sufficiently proximate to the groove in the plane of the substrate for an evanescent field of pump light propagating in the waveguiding channel to extend laterally into the groove; and filling the groove with a material capable of population inversion when exposed to pump light propagating in the second waveguiding channel and which produces stimulated emission at the resonant wavelength of the resonant cavity. Additionally, the method may further comprise: forming a pair of further grooves in the substrate such that the parts of the waveguiding channel having the pair of Bragg gratings are sufficiently proximate in the plane of the substrate to the pair of further grooves for an evanescent field of light propagating in the waveguiding channel to extend into the grooves; filling the pair of further grooves with liquid crystal; and providing electrodes by which electric fields can be applied across the liquid crystal to modify the Bragg wavelength of the Bragg gratings, and thereby tune the resonant wavelength.

In further embodiments, the optical waveguide device may be an amplifier, and the method may further comprise: forming a second waveguiding channel in the core layer for propagation of pump light, the second waveguiding channel having a part sufficiently proximate to the groove in the plane of the substrate for an evanescent field of pump light propagating in the waveguiding channel to extend laterally into the groove; and filling the groove with a material capable of population inversion when exposed to pump light propagating in the second waveguiding channel and which produces light by stimulated emission that couples into the said waveguiding channel for amplification of light propagating therein.

A second aspect of the present invention is directed to an optical waveguide device comprising: a planar substrate comprising at least a lower cladding layer, a core layer and an upper cladding layer; a groove formed in the substrate and having a depth extending at least into the core layer; and a waveguiding channel in the core layer; wherein at least a part of the waveguiding channel is sufficiently proximate to the groove in the plane of the substrate for an evanescent field of light propagating in the waveguiding channel to extend laterally into the groove.

The device may further comprise a Bragg grating in the part of the waveguiding channel proximate to the groove. The groove may have a depth extending to, into or through the lower cladding layer.

BRIEF DESCRIPTION OF THE DRAWINGS

For a better understanding of the invention and to show how the same may be carried into effect reference is now made by way of example to the accompanying drawings in which.

DETAILED DESCRIPTION

Conventionally, optical devices that exploit the effect of a sample of material on the evanescent optical field of light propagating in a waveguide comprise a window etched into the top surface of a planar substrate containing a channel waveguide. The window is positioned over the waveguide and extends down to or into the core layer of the substrate so that the evanescent field can extend into material contained in the window. The presence of a material in the window modifies the optical field. A material placed in the window can thereby be interrogated if the modification is measured; the amount of modification is representative of a property of the material which can hence be determined. A device operated in this way is therefore a sensor. Alternatively, the material properties can be used to deliberately modify the light in a desired manner, so that the device operates as a modulator. In all cases, however, the geometry of the waveguide and window combination is orthogonal to the plane of the substrate.

The present invention seeks to overcome some of the drawbacks of these devices and their geometry and fabrication by proposing an alternative geometry, in which the channel waveguide and the "window" are arranged side-by-side in the plane of the substrate and in close proximity so that the evanescent field extends into the "window" and the material therein in a lateral direction, through the side wall of the "window". Thus, assuming that the substrate is oriented horizontally, the device geometry is also horizontal, in contrast to the vertical configuration of existing devices.

The shallow surface window of the known devices is replaced according to the present invention by a groove, trench or channel formed in the substrate, which extends sufficiently deeply into the substrate that the optical field of light carried by a waveguiding channel formed in the core layer of the substrate and adjacent to the groove can extend into the groove (which will contain sample material or material to modify the propagating light). Thus, the groove will have a depth that extends at least part of the way into the core layer, and more probably all the way through the core layer and possibly into the underlying cladding layer or further. Complete exposure of the full thickness of the core layer by the side wall of the groove increases the amount of the evanescent field that can penetrate into the groove and therefore maximises the interaction between the light and any material in the groove. The waveguiding channel and the groove are sufficiently close together that a sufficient amount of the evanescent field overlaps into the groove to create a discernable optical path change for light propagating in the waveguide.

The proximity of the groove and the waveguide determines the sensitivity of the device; the sensitivity is higher if the core of the waveguide is in direct contact with the groove than if it is some distance away. To give an idea of scale, an example of a larger spacing between the edge of the groove and the centreline of the waveguide is 15 micrometers. Also, the sensitivity can be enhanced by reducing the width of the waveguide in the proximate region. The amount of reduction may depend in part on the ability of the waveguide to support an optical mode. Further, the optimal proximity of the waveguide relative to the groove is also determined by the absolute index and loss of the material in the groove, the interaction length between the groove and the waveguide, and the system used to analyse the light detected from the waveguide.

Figure 1A:
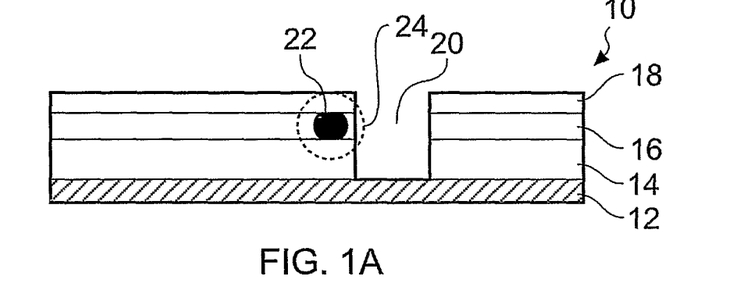
FIGS. 1A and 1B show respectively a cross-sectional side view and a plan view of an optical waveguide device according to an embodiment of the invention.

FIG. 1A shows a cross-sectional view through a substrate configured as an optical device in accordance with an embodiment of the invention. The device 10 is formed from a layered planar substrate comprising a base layer 12, a lower cladding layer 14 arranged over the base layer 12, a core layer 16 arranged over the lower cladding layer 14, and an upper cladding layer 18 arranged over the core layer 16. The core layer 16 has a higher refractive index than the cladding layers, to confine propagating light in accordance with the well-known principles of optical waveguiding. The device may comprise additional layers if desired.

A waveguiding channel or waveguide 22 (shown in end view in FIG. 1A) comprises a path of higher refractive index defined in the core layer 16 so that light is confined to the waveguide 22 in the plane of the core layer 16. Light propagating along the waveguide 22, although largely confined within the high refractive index region, also has an evanescent optical field 24 that extends beyond the waveguide 22.

The device 22 further comprises a groove or trench 20 defined in the substrate material, and in this example extending down through the upper cladding layer 18, the core layer 16 and the lower cladding layer 14 to the base layer 12. The groove 20 is roughly parallel to the waveguide 22 in the plane of the substrate. At the plane of the cross-section shown in FIG. 1, the waveguide 22 approaches very close to the groove 20 so that the optical field 24 extending out from the waveguide 22 reaches into the groove 20. Therefore, light propagating along the waveguide 22 can interact with any material contained in the groove 20 (none is shown in FIG. 1A).

Figure 1B:
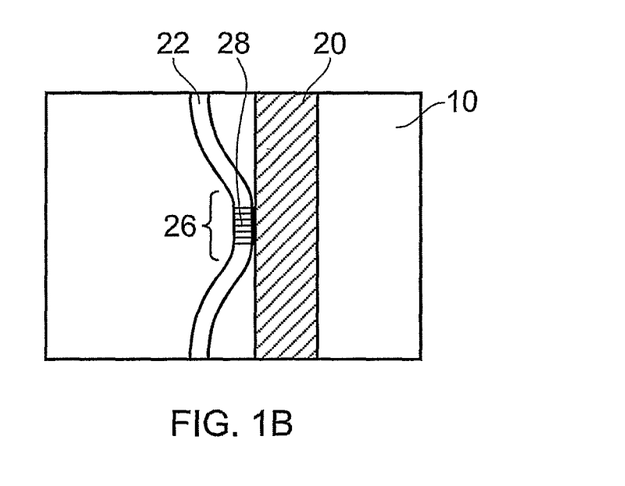

FIG. 1B shows a plan view of the device 10 shown in FIG. 1A. In this example, the groove 20 is straight and extends across the substrate. The waveguide 22, although generally parallel to the groove 10, has a slightly serpentine path which brings only a part 26 of the waveguide 22 into sufficiently close proximity with the groove 20 for the evanescent field to reach into the groove 20. The waveguide 22, initially more remote from the groove 20, curves towards the groove 20, runs parallel to it in close proximity for a short distance, and then curves away. Thus, optical interaction with material in the groove is limited to a small length 26 of the waveguide 22, giving a similar arrangement to that offered by a delimited overlying window in a conventional device.

However, the smooth curving relationship between the waveguide 22 and the groove 20 offers a significant advantage over the conventional surface window. The curves give a gradual adiabatic increase and decrease to the extension of the evanescent field into the groove and the material it contains. A window, in contrast, has sharply defined edges across the path of the waveguide, giving abrupt changes which cause unwanted back reflections and cavity effects. Thus, better quality light signals with lower loss can be obtained using a device according to the invention.

FIG. 1B also shows a Bragg grating 28 defined in the waveguide 22 at the part 26 proximate to the groove 20. Although not essential to the invention, a grating in the interaction region between the waveguide and the groove can provide various functions. For example, the device can be used to measure refractive index. The characteristic Bragg wavelength of the Bragg grating, being the peak wavelength at which the grating reflects, varies with the effective modal index experienced by light propagating in the grating. A material in the adjacent groove will modify that effective modal index, thereby altering the Bragg wavelength. This alteration or shift can be detected from light reflected from or transmitted by the grating, and used to calculate the refractive index of the material. Window-based sensors using this principle are known [1, 2]. Devices according to the present invention are not limited to including a grating in the position shown in FIG. 1B, and may or may not include Bragg gratings in the proximate region of the waveguide or elsewhere.

The groove and the waveguide may be formed by any convenient fabrication technique, with either formed first. A disadvantage of existing devices with surface windows is that the window must necessarily be formed after the waveguide, because of its position over the waveguide. The present invention is free from this constraint, and allows the groove to be fabricated before the waveguide if desired. In fact, this arrangement is highly advantageous because it allows the less intricate fabrication step to be performed first. Thus any errors that occur in making the groove do not result in the waste of previous effort in making the waveguide, as can occur for a window-based design.

The groove may conveniently be fabricated using a cutting device such as a saw or mill of the type used to dice and otherwise prepare wafers in the semiconductor industry. The saw cuts into the substrate to the required depth. The groove depth is by no means as critical as the depth requirement for a surface window (which defines the proximity to the waveguide), so less accuracy is needed and the comparatively coarse method of cutting or milling is sufficient. Cutting in this way is both quick and inexpensive compared to the time-consuming and costly acid etching technique for forming windows. Also, the highly corrosive and therefore dangerous hydrofluoric acid is eliminated. A further advantage is that the groove cutting can be combined with dicing of a large wafer into smaller device substrates to allow two fabrication steps to be performed together.

The spacing between the groove and the waveguide is important for good device operation. The positional errors likely in defining a groove or trench by cutting with a saw means that it is less appropriate for this technique to be used in cases where the waveguide is fabricated first, because it is more difficult to locate the groove with sufficient accuracy relative to the waveguide. Therefore, if the waveguide has already been fabricated, other methods of making the groove are more suitable. For example, lithographic techniques allow sufficiently accurate indexing of the groove position relative to the waveguide. Formation of the trench by lithography and etching may also be used in situations where the groove is made before the waveguide.

Similarly, any method can be used for forming the waveguide and any Bragg gratings therein. However, a particularly advantageous technique, and one which has been found to be highly compatible with using a saw to cut the groove, is that of direct ultraviolet writing [3].

This technique uses a beam of ultraviolet (UV) light, focussed to form a spot having a width matching that of the desired width of the waveguide, to trace the intended path of the waveguide through a region of photosensitive material. The exposure to UV light causes the refractive index of the photosensitive material to permanently increase, giving the higher refractive index value needed for the core of a waveguide. Thus, if the core layer of a substrate is made of photosensitive material, the UV spot can write a waveguide in the core layer. If the spot has a "constant" intensity distribution (such as Gaussian) and moves through the photosensitive material at a constant velocity, a uniform refractive index change is produced along the waveguide, giving a uniform waveguide. A similar effect results if the spot has a pattern of high and low intensity fringes but moves at a constant velocity. However, a fringed spot moved in a discontinuous manner, such as by exposing consecutive parts of the material in sequence, can produce a Bragg grating in the waveguide. Very fine control of the relative movement of the spot and the substrate is possible, allowing a complex pattern of waveguides with integral gratings to be written with a high degree of positional accuracy in a simple one-stage fabrication process.

The combination of the two simple techniques of cutting a groove with a saw and directly writing a waveguide with a UV spot gives a highly advantageous method for forming optical waveguide devices according to the present invention. In particular, the groove can be formed before the waveguide, which is preferable from the point of view of performing the least delicate fabrication step first. UV writing allows the waveguide to be formed second, which is more difficult with other waveguide fabrication techniques because the presence of the groove would prevent the successful spinning of resist onto the substrate surface. UV writing after groove formation also offers the ability to achieve sufficiently accurate positional alignment between the groove and the waveguide.

However, at first sight, it may appear that the combination of cutting a groove with a saw followed by direct UV waveguide writing would not produce good results. For example, the groove fabrication should not produce significant mechanical weakness, delamination, degradation or stress-induced birefringence in the substrate that could interfere with subsequent waveguide fabrication and operation. Cutting with a saw might cause these problems. Also, the close proximity of the waveguide path to the groove could produce interference with the UV writing beam or cause catastrophic material ejection. The vertical edge of the groove needs to be of sufficient quality not to generate scattering of the UV writing beam. Sufficiently accurate alignment between the groove and the waveguide needs to be achievable, preferably to a submicron level.

A useful method for alignment has been found to be that of monitoring the amount of light transmitted sideways into the groove from the UV writing beam. The magnitude of the measured light is proportional to the distance of the beam from the wall of the groove, so the UV spot can positioned accordingly. This has been found to provide a good level of positional accuracy. While the monitoring can be carried out throughout the writing process, it can also be performed initially at each end of the groove (by, for example, intersecting the foci of the two UV beams used to produce a fringed spot with the edge of the groove) to ensure that the axis of the groove and the axis of the translation stage used to produce relative movement between the substrate and the writing spot are collinear.

Sample devices have been fabricated to test the compatibility of cutting a groove followed by UV writing of a waveguide with gratings. A substrate with an area measuring 10 mm by 20 mm consisted of base layers supporting a thermally oxidized silicon lower cladding layer overlaid by two layers of silica deposited using flame hydrolyse deposition (FHD) providing the core layer and the upper cladding layer. The core layer was doped with germanium oxide to promote photosensitivity for the UV writing. Other dopants were also included to match the refractive indices as required. The photosensitivity of the core layer was further enhanced by leaving the substrate in a high pressure (approximately 120 bar) hydrogen environment for several days to load the substrate with hydrogen. This substrate is merely an example, however. The invention is applicable to any substrate in which a waveguide can be fabricated.

Grooves were cut into the substrate to a depth extending past the lower cladding layer using a semiconductor dicing saw. The grooves were 300 μm deep and 300 μm wide. This is relatively large, to allow adequate testing for mechanical weakness and any delamination problems.

Waveguides and Bragg gratings were then formed using the UV direct writing technique described above and in WO 2004/049024 [3]. A frequency-doubled argon ion laser generated 244 nm wavelength writing light with a power range of 50 to 100 mW and fluencies in the range 1 to 20 kJ/cm$^2$.

Figure 2A:
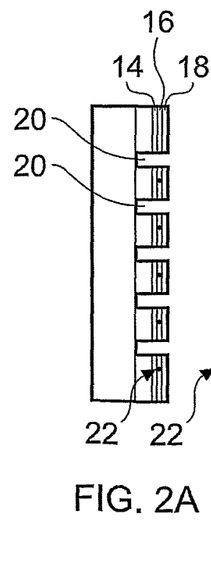
FIGS. 2A and 2B show respectively a side view and a plan view of a sample optical waveguide device fabricated in accordance with an embodiment of the invention.
Figure 2B:
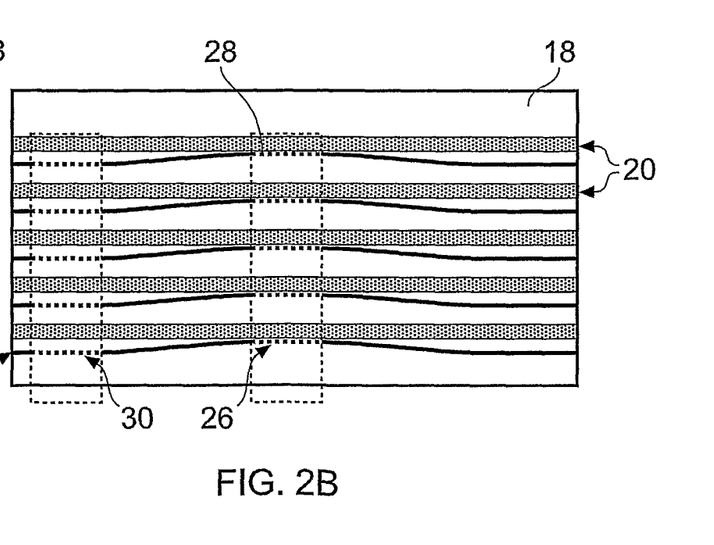

FIGS. 2A and 2B show a side view and a plan view of the substrate after groove and waveguide fabrication. The side view shows the lower cladding layer 14, the core layer 16 and the upper cladding layer 18. Five grooves or trenches 20 are cut into the substrate, and five waveguides 22 (shown in end view in FIG. 2A) are defined, one next to each groove.

The plan view FIG. 2B shows the grooves 20 extending the length of the substrate (not essential but this makes for easier fabrication with a saw), with the associated waveguides 22 running alongside the grooves 20 and each having a portion 26 that approaches closely to the associated groove 20. In this example, each proximate portion 26 contains a Bragg grating 28. Also in this example, each waveguide 22 includes a second Bragg grating 30 defined in a part of the waveguide 22 that is not proximate to the groove 20. These second gratings 30, which are unaffected by any material in the nearby groove, can be used as reference gratings to compensate for any environmental factors such as temperature which may cause wavelength shifts in the primary Bragg gratings which would be otherwise indistinguishable from the shift caused by the material. Each groove-grating pair could, for example, be used as a refractive index sensor. A single pair might be provided on one substrate, but the invention is flexible in allowing multiple waveguides, gratings and grooves to be easily fabricated on the same substrate. The configuration of FIGS. 2A and 2B could therefore be used for simultaneously measurements of five different samples, or for simultaneous measurements at five different wavelengths if the gratings have different Bragg gratings.

Characterisation tests on the sample of FIGS. 2A and 2B showed no stress-induced birefringence, and further suggested that the grooves actually reduce stress-induced birefringence as compared to devices with surface windows. Similar effects have been observed elsewhere [7, 8]. Also, it was concluded that the reduction in stress via the definition of the grooves may increase the UV-induced refractive index change. Forming grooves in optoelectronic samples is not unknown, however, including by sawing and milling, and is carried out for functions such as alignment (so-called V-grooves), stress relief and waveguide formation [9-11].

It has been previously observed that UV writing into an absorbing layer such as the photosensitive core layer can cause surface ablation which can be catastrophic. It is known experimentally that defects on silica-on-silicon surfaces can cause UV absorption that leads to damage. Prior to fabrication of the substrate in FIGS. 2A and 2B, it was unclear if UV writing close to the side wall of the groove would cause material ejection into the groove. Low optical loss was measured from the waveguides 22, which suggests that any such ablation does not occur.

A concern relating to the use of a polishing/dicing saw is that of surface roughness in the walls of the grooves. It might be expected that scatter from the sawn surface would make UV waveguide writing untenable. The fact that this is not so is surprising. Also, as the waveguide approaches closer to the groove, the optical power reflected from the grating is reduced owing to the power lost into the groove, but the grating sensitivity increases. Optimisation of the proximity to balance these effects is dependent on the device requirements. However, the loss observed from the substrate of FIGS. 2A and 2B is comparable to that observed in devices with windows fabricated using surface acid etching. This indicates that any surface roughness and chipping of corners of the groove is not so significant as to prevent useful device operation.

Therefore, a quality device having a lateral geometry according to the present invention can be conveniently fabricated using groove formation with a saw followed by waveguide formation by direct UV writing.

Devices according to the present invention offer further advantages, including the adiabatic change offered by curving waveguides mentioned above. In addition, there is the ability to change the optical mode size in the lateral direction, by varying the width of the waveguide which can be easily achieved using UV writing. This also allows multimode operation, from which further information can be obtained about a sample material in the groove if the device is configured as a sensor. Also, it is possible for a single waveguide to have multiple regions that are proximate to a single groove, each region having a different proximity. This allows different penetration depths of the evanescent mode into the groove, so that multiple measurements can be simultaneously made on a single sample of material. Different grating wavelengths can be used to distinguish the different proximities. Additionally, the lateral arrangement of waveguide and groove allows separate waveguides to access the same groove (and any material therein), by placing a waveguide on each side of the groove. Indeed, the lateral configuration is highly flexible, allowing complex groupings of individual grooves and waveguides. A wide variety of sensor and modulator devices can thereby be achieved, including the desirable design of multiple sensors on a single chip.

The example device shown in FIGS. 2A and 2B is very simple. The invention can be readily extended to a wide variety of devices.

Figure 3:
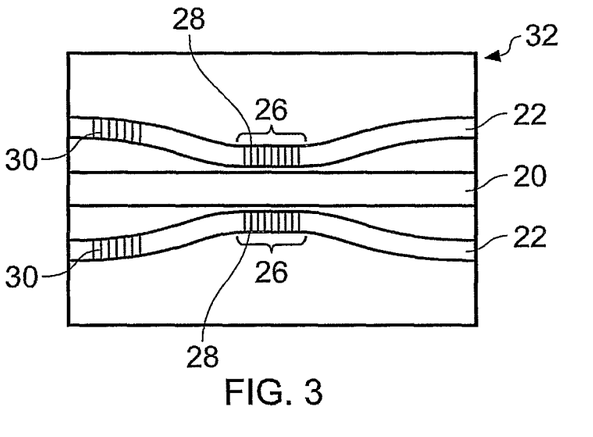
FIG. 3 shows a plan view of a sensor device according to an embodiment of the invention.

FIG. 3 shows a plan view of an alternative device. In this example, the device 32 comprises a single groove 20 and two waveguides 22. The waveguides 22 are arranged one on each side of the groove 20, and each has one region 26 that is proximate to the groove 20, and includes a Bragg grating 28. Also, each waveguide 22 includes a secondary or reference grating 30 located in a part of the waveguide remote from the groove, as described with respect to FIG. 2B. The proximate gratings 28 may be used for refractive index measurements, with compensation for environmental disturbances provided by the reference gratings 30. The provision of two separate waveguides to access the same groove, and hence the same sample of material, allows redundancy and confirmation for the refractive index measurement. The width of the groove 20 should be sufficient to avoid coupling of the optical fields between the waveguides 22.

Figure 4:
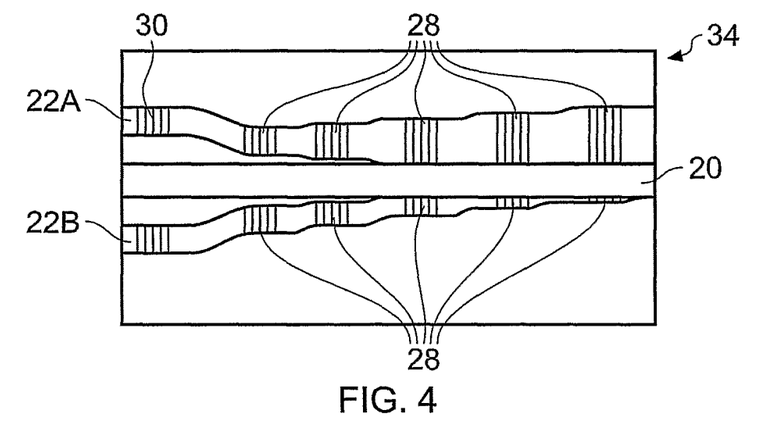
FIG. 4 shows a plan view of an alternative sensor device according to a further embodiment of the invention.

FIG. 4 shows a plan view of a further example device. The device 34 again features a single groove 20 extending across the substrate and two waveguides 22, one on each side of the groove 20. Again, each waveguide 22 includes a reference grating 30 in a part of the waveguide remote from the groove 20. In this example, however, each waveguide 22 includes a plurality of gratings 28 that are proximate to the groove 20. One waveguide 22A has a width that varies with distance along the waveguide/groove. This allows higher order optical modes to propagate. Each grating 28 is arranged in a portion of the waveguide 22A having a different width, and each grating 28 has a different Bragg wavelength. This provides a way of interrogating the refractive index of a sample in the groove 20 at each of the modes. The larger cross-section of the higher order modes may give additional information about the index variation of the sample material.

The other waveguide 22B has a constant width, but is arranged such that each of its plurality of gratings 28 has a different proximity to the groove 20. The evanescent field can therefore penetrate further into the groove for each successive grating. The gratings 28 have different Bragg wavelengths so that they can be distinguished, and in addition the combination of different period gratings with different proximities/penetration depth provides a high level of sensitivity for samples of different refractive index. This configuration also reduces the mechanical tolerances on fabrication.

Although the device in FIG. 4 includes two differently configured waveguides each with several gratings, which together offer a wide range of index measurements from a single device, a device including just one or the other of the waveguides may instead be provided.

Figure 5:
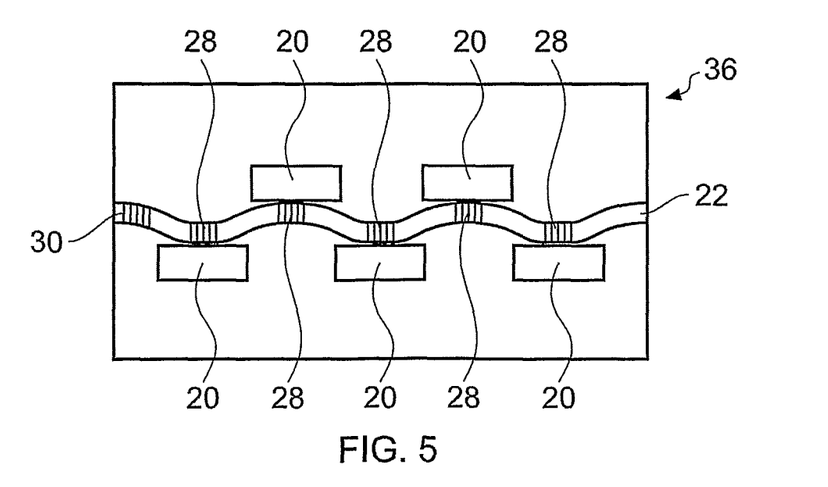
FIG. 5 shows a plan view of a further alternative sensor device according to a yet further embodiment of the invention.

FIG. 5 shows a plan view of another example device. The device 36 comprises a single waveguide 22 having a reference grating 30 at one end. In contrast to the previous examples, a plurality of individual separate grooves 20 is formed in the substrate. The waveguide 22 is shaped to come into proximity with each of the grooves, so that the waveguide 22 follows a serpentine or undulating path. The waveguide 22 has a plurality of gratings 28, one in each waveguide section that is proximate to a groove 20. This allows a plurality of samples to be analysed at the same time from a single waveguide, by a different sample being placed in each groove 20. Alternatively or additionally, each groove may be provided with a different surface treatment to interact with the sample material; this provides information on different components of a sample material. In an alternative arrangement, the waveguide may be substantially straight, and each of the grooves may be curved into and out of proximity with the waveguide.

Figure 6:
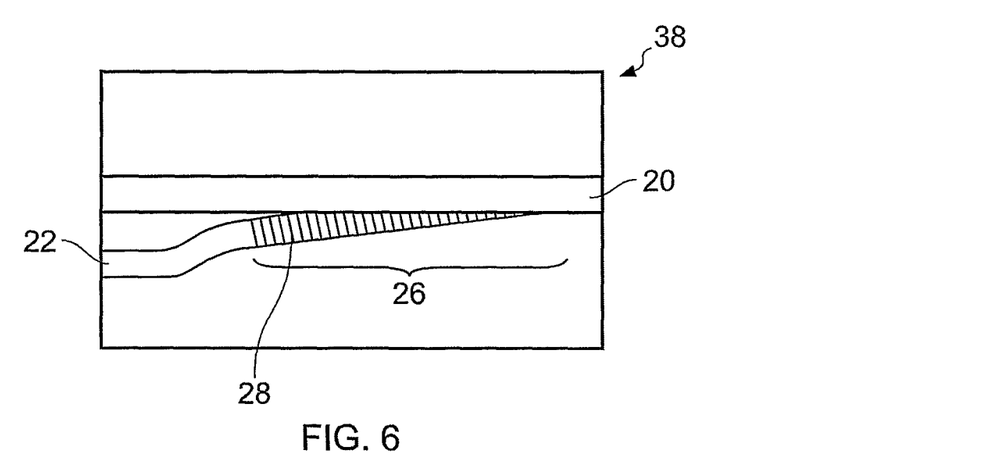
FIG. 6 shows a plan view of a still further alternative sensor device according to a still further embodiment of the invention.

FIG. 6 shows a plan view of another device 38. This includes just one groove 20 and one waveguide 22. However, the portion 26 of the waveguide 22 that is proximate to the groove 20 is arranged at an angle to the axis of the groove so that the waveguide tapers along its length, with a decreasing width. Thus, the proximity of the waveguide, and the penetration of the evanescent wave, increases with distance along the proximate part 26 of the waveguide 22. In addition, the proximate part 26 includes a Bragg grating 28, which in this example is chirped, i.e. it has a grating period that varies with distance along the grating. The grating period and the proximity are related along the grating 28. A change in index yields a change in the bandwidth of the light reflected by the grating 28, making it insensitive to temperature fluctuations. Monitoring of the bandwidth of the reflected spectrum 28 therefore gives a temperature-insensitive measurement of the refractive index of a sample material in the groove 20 (hence the device 38 does not include a reference grating 38). The use of chirped gratings to obtain temperature-independent measurements of strain is known [12], but it is believed that a refractive index sensor using chirp to compensate for temperature as proposed herein is novel.

The use of a continuously varying evanescent wave penetration depth is made possible by the lateral arrangement proposed by the present invention. Such variation is difficult if not impossible to achieve with any precision using a surface window overlying a waveguide grating. The increased control over the spacing between the waveguide and the groove that is made possible by a lateral configuration is highly advantageous and offers much flexibility in device design.

Figure 7:
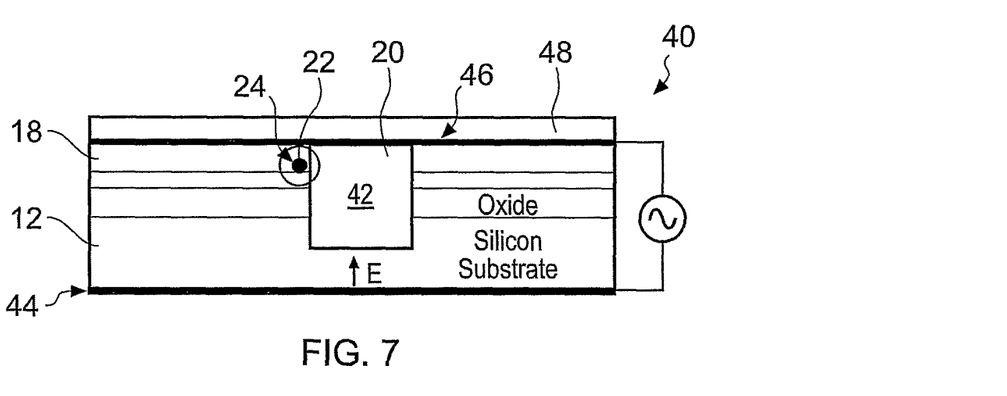
FIG. 7 shows a cross-sectional side view of a modulator device according to an embodiment of the invention.

FIG. 7 shows a cross-sectional view of a further alternative device, which can be operated as a modulator, in contrast to the sensors described so far. The device 40 again comprises a waveguide 22 in close proximity to a groove 20 so that the optical field 24 of the waveguide 22 extends into the groove 20. A Bragg grating is included in the proximate region of the waveguide 22. In this example, however, the groove 20 is filled with an active material rather than a sample analyte material. Liquid crystal 42 or another tunable dielectric material may be used, for example, to provide modulation of an optical signal propagating in the waveguide 22. To achieve modulation, an electric field is applied across the liquid crystal 42. The resulting change to the refractive index of the liquid crystal 42 changes the Bragg wavelength of the grating via the effect on the evanescent optical field 24. Thus, the grating can be tuned. A pair of electrodes arranged across the liquid crystal 42 is required for application of the electric field. This can be facilitated by use of the silicon substrate layer as an electrode. As shown in FIG. 7, the groove 20 containing the liquid crystal 42 extends down into the substrate base layer 12, which is made of silicon, and is provided with an aluminium contact 44 on its lower surface so that it can function as an electrode. A second electrode is provided by a thin film 46 of indium tin oxide (ITO) on the lower surface of a sheet of glass 48 or similar that is placed over the upper cladding layer 18 of the device 40 to contain the liquid crystal 42.

Figure 8:
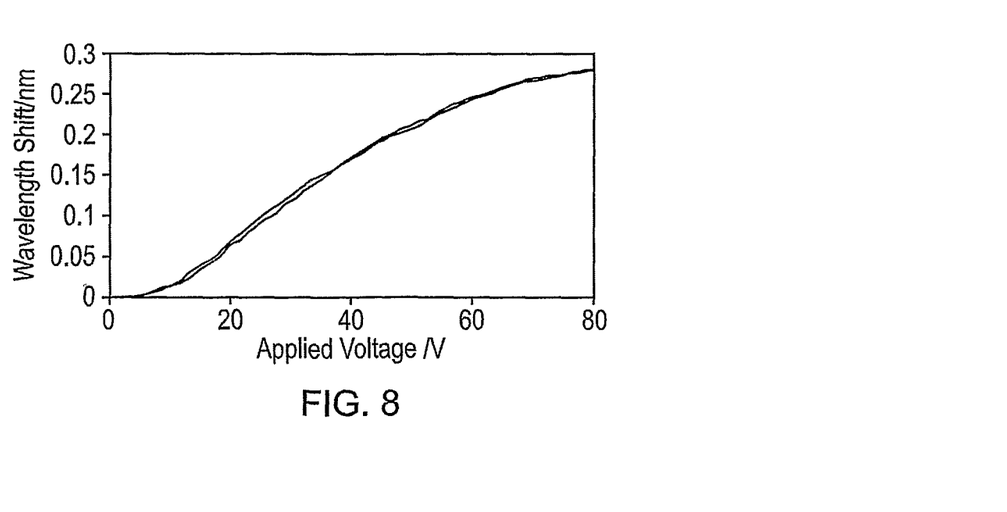
FIG. 8 shows a graph of wavelength shift produced by varying a voltage applied to the modulator device of FIG. 7.

FIG. 8 shows a graph of results obtained from the modulator 40 of FIG. 7, illustrating the wavelength shift obtained as a function of applied voltage.

The modulator of FIG. 8 may be extended by providing a second waveguide on the other side of the groove 20, with a similar geometry to that of FIG. 3, and a groove width in the range of about 5 to 20 μm. This provides a controllable coupler, in which the amount of optical coupling from one waveguide to the other across the groove (which is narrow enough for this to occur) is modifiable according to the voltage applied across the liquid crystal. A similar device based on side-polished fibres has been proposed [13], but is extremely time-consuming and expensive to fabricate.

Figure 9:
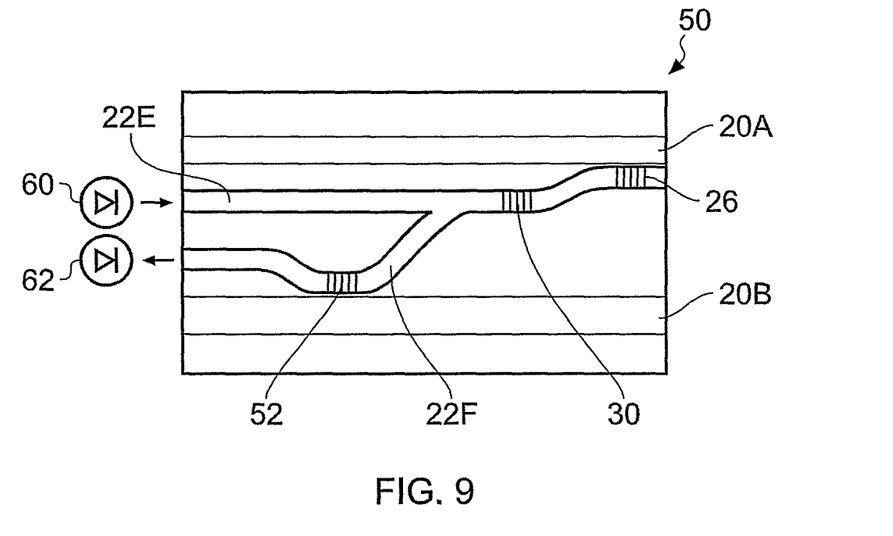
FIG. 9 shows a plan view of a device according to an embodiment of the invention, incorporating a sensor and a modulator.

FIG. 9 shows a plan view of a device 50 that combines a refractive index sensor and a tunable modulator. The substrate is provided with two grooves 20A, 20B spaced apart from one another. One groove 20A receives a sample of analyte material, and the other groove 20B is filled with liquid crystal or another tunable dielectric, suitable electrodes being provided for application of an electric field across the liquid crystal. An input waveguide 22E has a section proximate to the analyte groove 20A which includes a grating 26 so that the refractive index of the analyte material can be sensed. Light reflected from the grating 26 is directed along an output waveguide 22F that branches off from the input waveguide 22E. The output waveguide 22F has a section including a grating 52 which is proximate to the liquid crystal groove 20B. The response of the grating 52, in particular its transmission wavelength, can be tuned by varying the voltage applied across the liquid crystal, thereby providing a tunable filter. Tuning this output grating 52 in a known manner allows the reflection spectrum of the sensor grating 26 to be analysed, i.e. by tuning the output grating 52 and measuring the amount of light reflected from the sensor grating 26 that is transmitted, the full spectrum of the reflected light can be easily measured, from which the refractive index of the analyte material can be determined. The device may also include a temperature reference grating 30 in a part of the input waveguide 22E that is remote from the analyte groove 20A but from which reflected light can travel to the output waveguide 22F; this may also be analysed by tuning the output grating 52.

The modulator thus acts as an analyser of the index sensor. Butt-coupling a broadband diode optical source 60 to the waveguide input and a photodiode 62 to the waveguide output provides a cheap, compact refractive index sensor.

Figure 10:
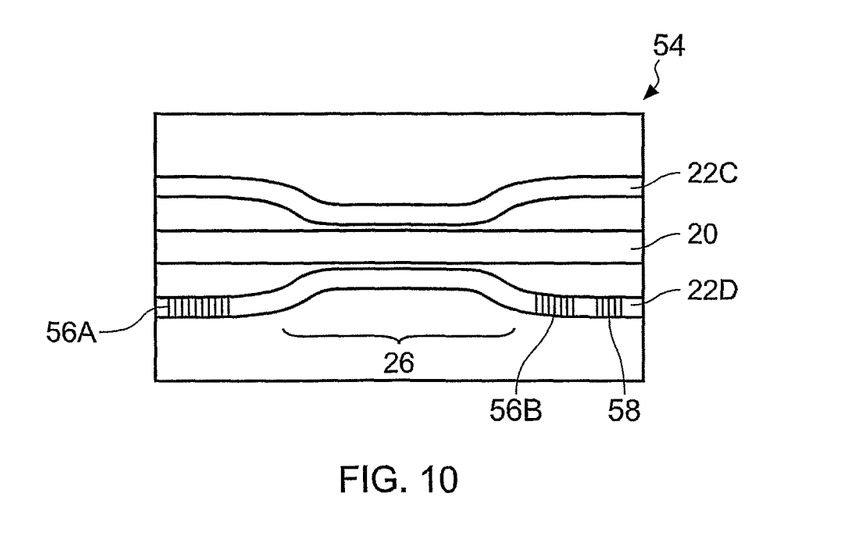
FIG. 10 shows a plan view of a laser device according to an embodiment of the invention.

FIG. 10 shows a plan view of a device that can be operated as a laser. The device 54 includes a single groove 20, and two waveguides 22C, 22D arranged one on each side of the groove 20, and each having a region that approaches proximate to the groove 20, similar to the arrangement of the device 32 of FIG. 4. In this example, however, one waveguide 22C has no Bragg gratings. The other waveguide 22D has a pair of Bragg gratings 56 with substantially the same Bragg wavelength. These gratings 56 are positioned in the waveguide 22D one on each side of the proximate region 26, i.e. the gratings are not proximate to the groove.

If the groove 20 is filled with a material capable of population inversion, such as Rhodamine 6G or another laser dye, the device 54 can operate as a laser. The waveguide 22C without gratings can propagate pump light that couples into the groove at the proximate region, and excites the laser material to produce an inversion. The stimulated emission from the laser material then couples across into the second waveguide 22D, where the two Bragg gratings 56 form a resonant laser cavity. The Bragg wavelength is therefore selected for the gratings to be suitably reflective at the laser wavelength. One grating 56A is a high reflector, and the other grating 56B has a lower reflectivity so as to act as an output coupler and transmit some of the laser light out along the waveguide 22D. An additional Bragg grating 58 that is reflective at the pump wavelength can be provided in the second waveguide 22D beyond the output coupler 56B to filter out any pump light that may couple across from the pump waveguide 22C to the laser waveguide 22D.

Tuning of the laser output wavelength can be achieved by altering the cavity grating wavelengths by localised heating or modulation by liquid crystal in a proximate groove as described with regard to FIG. 7. Alternatively, the cavity gratings 56 can be replaced by broadband reflectors on the end facets of the waveguide 22D to provide a larger tuning range. Also, the gain medium material in the groove could be replaced by a material with a strong Raman effect to provide a Raman-shifted laser.

Laser devices such as these are potentially very useful as building blocks for so-called "lab on a chip"-type experiments.

Moreover, if the cavity gratings 56 are omitted, a similar arrangement can be used as an optical amplifier to amplify light at the "laser wavelength" that is already propagating in the second waveguide 22D.

For devices configured as sensors, samples of fluid can be delivered to the groove or grooves by a microfluidic system. The grooves can be connected by channels in the substrate surface to form a fluid network, though which a fluid can flow. The network be closed (to contain the fluid) by a sealing layer (or glass or Perspex, for example) laid over the top surface of the sensor, with input and output access points for fluid to be injected into the network and then removed therefrom. A gasket layer under the sealing layer can improve the sealing of the fluid network, for example to enhance suction of fluid through the network or to reduce sample contamination.

Thus, a wide variety of optical waveguide devices can be made that exploit the inventive concept of a proximate and laterally arranged waveguide and groove in the same substrate. The invention is not limited to the examples described herein; many other examples will be apparent to the skilled person.

REFERENCES

[1] WO 2006/008447
[2] WO 2006/008448
[3] WO 2004/049024
[4] I J G Sparrow, G D Emmerson, C B E Gawith et al, Sensors and Actuators B—Chemical, vol 107(2), p 856, 2005
[5] I J G Sparrow, G D Emmerson, C B E Gawith et al, Applied Physics B—Lasers and Optics, vol 81(1), p 1, 2005

[6] I J G Sparrow, G D Emmerson, C B E Gawith et al, IEEE Photonics Technology Letters, vol 17(2), p 438, 2005
[7] Y Nasu, M Kohtoku, M Abe et al, Electronics Letters, vol 41 (20), p 1118, 2005
[8] Y Inoue, K Katoh and M Kawachi, IEEE Photonics Technology Letters, vol 4(1), p 36, 1992
[9] M Iwai, T Yoshino, S Yamaguchi et al, Applied Physics Letters, vol 83 (18), p 3659, 2003
[10] S Kurimura, Y Kato, M Maruyama et al, Applied Physics Letters, vol 89(19), article 191123, 2006
[11] K Mizuuchi, T Sugita, K Yamamoto et al, Optics Letters, vol 28(15) p 1344, 2003
[12] A D Kersey, M A Davis, H J Patrick et al, Journal of Lightwave Technology, vol 15 (8), p 1442, 1997
[13] R P Pan, S R Liou and C K Lin, Japanese Journal of Applied Physics Part 1—Regular Papers, Short Notes & Review Papers, vol 35(12A), pp 6410-6415, 1995

The invention claimed is:

1. A method of fabricating an optical waveguide device, comprising:
providing a planar substrate comprising at least a lower cladding layer, a core layer and an upper cladding layer;
forming in the substrate:
a groove having a depth extending at least into the core layer; and
a waveguiding channel in the core layer;
in which the groove is formed before the waveguiding channel is formed, and wherein at least a part of the waveguiding channel is substantially parallel to the groove and sufficiently proximate to the groove in the plane of the substrate for an evanescent field of light propagating in the waveguiding channel to extend laterally into the groove; and
forming a Bragg grating in the part of the waveguiding channel proximate to the groove.

2. A method according to claim 1 in which the core layer is photosensitive, and the waveguiding channel and the Bragg grating is formed by exposing parts of the core layer to a spot of ultraviolet light to produce a change in refractive index.

3. A method according to claim 2, in which the spot of ultraviolet light has a periodic intensity pattern of high and low intensity fringes.

4. A method according to claim 2, in which the position of the spot of ultraviolet light relative to the groove in the plane of the substrate is tested during formation of the waveguiding channel by measuring the amount of light transmitted from the spot into the groove.

5. A method according to claim 1, in which the groove is formed using a cutting device.

6. A method according to claim 5, in which the cutting device is a semiconductor wafer dicing or milling saw.

7. A method according to claim 1, further comprising forming one or more further waveguiding channels in the core layer, and wherein at least a part of the or each further waveguiding channel is sufficiently proximate to the groove in the plane of the substrate for an evanescent field of light propagating in the further waveguiding channel to extend laterally into the groove.

8. A method according to claim 7, further comprising forming a Bragg grating in the part of each waveguiding channel proximate to the groove.

9. A method according to claim 1, further comprising forming one or more further grooves in the substrate, the or each groove having a depth extending at least into the core layer, and wherein the waveguiding channel has parts sufficiently proximate in the plane of the substrate to every groove for an evanescent field of light propagating in the waveguiding channel to extend into the grooves.

10. A method according to claim 9, further comprising forming a Bragg grating in each part of the waveguiding channel proximate to a groove.

11. A method according to claim 1, in which the waveguiding channel has at least two parts sufficiently proximate to the groove in the plane of the substrate for an evanescent field of light propagating in the waveguiding channel to extend into the groove, each proximate part having a different proximity to the groove.

12. A method according to claim 1, in which the waveguiding channel has at least two parts sufficiently proximate to the groove in the plane of the substrate for an evanescent field of light propagating in the waveguiding channel to extend into the groove, each proximate part having a different width.

13. A method according to claim 1, in which the Bragg grating is a chirped Bragg grating, and the waveguiding channel is formed such that the part proximate to the groove has a proximity that varies as a function of the grating period.

14. A method according to claim 1, in which the optical waveguide device is an optical modulator, the method further comprising filling the groove with liquid crystal and providing the substrate with electrodes by which an electric field can be applied across the liquid crystal to modify the Bragg wavelength of the Bragg grating.

15. A method according to claim 1, in which the optical waveguide device is a refractive index sensor, the method further comprising: forming a second groove in the substrate, filling the groove with liquid crystal and providing the substrate with electrodes by which an electric field can be applied across the liquid crystal; forming a second waveguiding channel arranged to collect light reflected from or transmitted by the Bragg grating in the said waveguiding channel, the second waveguiding channel having a portion sufficiently proximate to the second groove in the plane of the substrate for an evanescent field of light propagating in the second waveguide to extend laterally into the second groove; and forming a second Bragg grating in the proximate part of the second waveguiding channel such that application of an electric field across the liquid crystal can modify the Bragg wavelength of the second Bragg grating.

16. A method according to claim 1, in which the optical waveguide device is a laser, the method further comprising: forming a pair of Bragg gratings in the waveguiding channel, one on each side of the part proximate to the groove, to define a resonant cavity in the waveguiding channel; forming a second waveguiding channel in the core layer for propagation of pump light, the second waveguiding channel having a part sufficiently proximate to the groove in the plane of the substrate for an evanescent field of pump light propagating in the waveguiding channel to extend laterally into the groove; and filling the groove with a material capable of population inversion when exposed to pump light propagating in the second waveguiding channel and which produces stimulated emission at the resonant wavelength of the resonant cavity.

17. A method according to claim 16, further comprising: forming a pair of further grooves in the substrate such that the parts of the waveguiding channel having the pair of Bragg gratings are sufficiently proximate in the plane of the substrate to the pair of further grooves for an evanescent field of light propagating in the waveguiding channel to extend into the grooves; filling the pair of further grooves with liquid crystal; and providing electrodes by which electric fields can be applied across the liquid crystal to modify the Bragg wavelength of the Bragg gratings, and thereby tune the resonant wavelength.

18. A method according to claim 1, in which the optical waveguide device is an amplifier, the method further comprising: forming a second waveguiding channel in the core layer for propagation of pump light, the second waveguiding channel having a part sufficiently proximate to the groove in the plane of the substrate for an evanescent field of pump light propagating in the waveguiding channel to extend laterally into the groove; and filling the groove with a material capable of population inversion when exposed to pump light propagating in the second waveguiding channel and which produces light by stimulated emission that couples into the said waveguiding channel for amplification of light propagating therein.

* * * * *

UNITED STATES PATENT AND TRADEMARK OFFICE
CERTIFICATE OF CORRECTION

PATENT NO. : 8,538,207 B2  Page 1 of 1
APPLICATION NO. : 12/596105
DATED : September 17, 2013
INVENTOR(S) : Gates et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 900 days.

Signed and Sealed this
Fifteenth Day of September, 2015

Michelle K. Lee
*Director of the United States Patent and Trademark Office*